United States Patent [19]

Asselineau et al.

[11] Patent Number: 5,242,550
[45] Date of Patent: Sep. 7, 1993

[54] PROCESS FOR THE SEPARATION OF BUTANES AND BUTENES BY EXTRACTIVE DISTILLATION

[75] Inventors: Lionel Asselineau, Paris; Paul Mikitenlo, Noisy le Roi, both of France

[73] Assignee: Institut Francais du Petrole, Rueil Malmaison, France

[21] Appl. No.: 840,976

[22] Filed: Feb. 26, 1992

[30] Foreign Application Priority Data

Feb. 26, 1991 [FR] France .................. 91 02385

[51] Int. Cl.$^5$ .............................. B01D 3/34
[52] U.S. Cl. ........................ 203/58; 203/26; 203/60; 203/78; 203/80; 585/809; 585/865; 585/866
[58] Field of Search ............ 203/58, 60, 26, 78, 203/27, 80, DIG. 8, DIG. 9; 585/860, 865, 809, 866, 864

[56] References Cited

U.S. PATENT DOCUMENTS

| | | | |
|---|---|---|---|
| 3,769,217 | 10/1973 | Bannister et al. | 203/80 |
| 3,772,158 | 11/1973 | Sarno | 203/65 |
| 3,890,208 | 6/1975 | Henneberg | 203/62 |
| 4,038,156 | 7/1977 | Knott et al. | 203/80 |
| 4,057,995 | 11/1977 | Kleiss | 203/1 |
| 4,162,198 | 7/1979 | Stockburger et al. | 203/80 |
| 4,163,697 | 8/1979 | Michaux | 203/80 |
| 4,419,188 | 12/1983 | McCall | 203/84 |
| 4,545,895 | 10/1985 | Brand et al. | 203/78 |
| 4,556,461 | 12/1985 | Ogura et al. | 203/38 |
| 4,718,986 | 1/1988 | Comiotto et al. | 203/38 |
| 4,777,321 | 11/1988 | Harandi et al. | 203/14 |

FOREIGN PATENT DOCUMENTS 0216991 4/1987 European Pat. Off. .

OTHER PUBLICATIONS

S. Ogura, T. Onda, Advances in C$_4$ Hydrocarbon Processing AICHE 1987 Summer National Meeting, Aug. 16-19, 1987.

Primary Examiner—Virginia Manoharan
Attorney, Agent, or Firm—Millen, White, Zelano & Branigan

[57] ABSTRACT

For the separation of butanes and butenes by extractive distillation, a charge mainly containing butanes and butenes is contacted in an extractive distillation column under pressure with a polar solvent (e.g., dimethyl formamide), the butanes being collected at the head. The solvent containing the butenes passes into a second column under pressure, where the butenes are partly desorbed and collected at the head. The solvent still containing butenes is purified in a third column under atmospheric pressure and the solvent-containing vapor distillate thereof is returned, after compression, to the lower part of the second column.

13 Claims, 1 Drawing Sheet

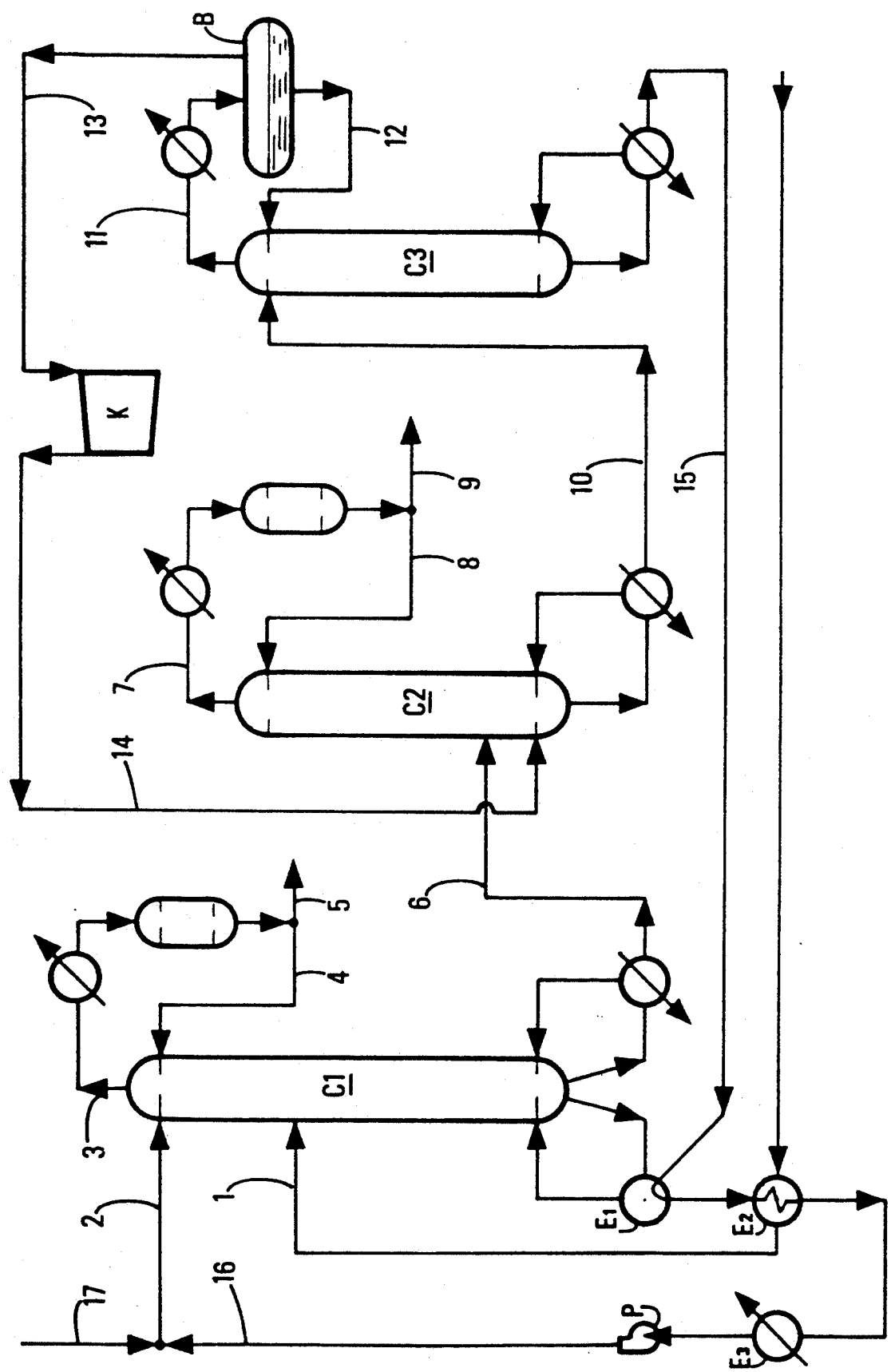

PROCESS FOR THE SEPARATION OF BUTANES AND BUTENES BY EXTRACTIVE DISTILLATION

BACKGROUND OF THE INVENTION

The invention relates to a process for the separation of butanes and butenes by extractive distillation.

In the treatment of the $C_4$ fraction resulting from steam or catalytic cracking, the separation of the butenes and butanes normally takes place downstream of the extractive distillation of the 1,3-butadiene and the methyl tert. butyl ether (MTBE) synthesis unit. Thus, a $C_4$ fraction is obtained, which is free from 1,3-butadiene and highly depleted in isobutene.

As butenes are valuable products, it is necessary to separate them from the butanes. Thus, the butenes can themselves be separated into 1-butene and 2-butenes, or can be isomerized into isobutene, which is recycled in the MTBE synthesis unit. The butenes can also be dimerized by the Dimersol (registered trademark) process into products usable in gasoline. This dimerization is a process performed by homogeneous catalysis, in which the catalyst is lost. As the efficiency of the catalyst is proportional to its concentration in the charge, a paraffin-free charge leads to considerable catalyst economies. Moreover, the butenes which have not reacted can be recycled if the butanes have previously been removed from the charge.

It is known to separate the butanes and butenes in a $C_4$ fraction by extractive distillation. A process has already been described (S. Ogura, T. Onda, Advances in $C_4$ Hydrocarbon Processing AIChE 1987 Summer National Meeting, Aug. 16-19, 1987) consisting of performing the extractive distillation under pressure with dimethyl formamide (DMF) as the solvent, solvent recovery being performed under atmospheric pressure and the purification of the butenes taking place under pressure. The bottom product of the extractive distillation column is fed into a column under atmospheric pressure, where the butenes are desorbed and leave at the column head with part of the solvent, whilst the bottom product is constituted by substantially pure DMF. The head butenes are then supplied for purification purposes to a pressure column. The solvent recovered at the bottom of the latter column and which still contains butenes returns to the atmospheric column.

The disadvantage of working according to this process is that most of the butenes of the charge have to be distilled twice which, bearing in mind the necessary recompression of the vapors of the butenes, leads to a high energy consumption.

SUMMARY OF THE INVENTION

A new process has now been discovered for the separation of butenes and butanes by extractive distillation and which has the advantage of avoiding the double distillation of the butenes of the charge and which only requires a limited recompression of the vapors of the butenes.

Like the prior art process described hereinbefore, the process according to the invention comprises an extractive distillation stage under pressure, but the solvent regeneration and butene purification stages are performed differently, as will be shown hereinafter.

The process for the separation of butanes and butenes according to the invention can be defined, in general terms in that the charge containing the butanes and butenes to be separated is introduced into an extractive distillation column under pressure, where it is contacted with a polar solvent in which the butenes have a higher volatility than the butenes, the distillate passing out at the head consisting essentially of the separated butanes. The residue collected at the bottom and which mainly consists of solvent and butenes, is passed into a pressure column, where the bottom temperature is adjusted in such a way that the desorption of the butenes is not complete, which makes it possible to limit the column bottom temperature and consequently avoid thermal decomposition of the solvent.

The solvent passing out at the bottom and which contains a fraction of the butenes is passed into a purification column under a pressure close to atmospheric pressure and whose operation is regulated in such a way that the head vapor, mainly constituted by butenes, also contains a fraction of the solvent, which makes it possible to partly condense it in order to ensure the reflux of the column, avoiding compression at this stage. The vapor distillate is passed, following compression, into a pressure desorption column. The purified solvent passing out at the bottom is recycled to the extractive distillation column.

The charge to be treated is generally a catalytic cracking or steam cracking $C_4$ fraction, from which the 1,3-butadiene has been removed, e.g., by extractive distillation and whose isobutene content may have been reduced, e.g., in a MTBE synthesis unit.

Thus, the charges in question mainly contain butenes (1-butene, cis 2-butene and trans 2-butene), n-butane, isobutane, isobutene in a small proportion and, in the state of traces, hydrocarbons having 3 to 5 carbon atoms.

More specifically, the charge composition can, e.g., be:

| | |
|---|---|
| Isobutane | 15 to 20% by weight |
| N-butane | 7 to 15% by weight |
| 1-butene | 20 to 25% by weight |
| Isobutene | <5% by weight |
| Trans 2-butene | 25 to 30% by weight |
| Cis 2-butene | 15 to 20% by weight |

The solvent to be used in the process according to the invention can be any selective polar solvent, i.e., in which the butanes have a higher volatility than the butenes. As non-limitative examples reference is made to monomethyl formamide, dimethyl formamide, diethyl formamide, dimethyl acetamide and N-methyl pyrrolidone. Dimethyl formamide is most frequently used.

BRIEF DESCRIPTION OF THE DRAWING

The process according to the invention will be described in greater detail hereinafter in conjunction with the attached drawing, which schamatically shows a simplified arrangement for its performance.

DETAILED DESCRIPTION OF THE DRAWING

The charge to be treated, previously heated to a temperature of 50° to 70° C., for example, through the exchanger E2, is introduced by the line 1 into the extractive distillation column C1 under a pressure of 4 to 10 bars.

The extraction solvent, at a temperature below its boiling point at the pressure in question, is introduced by the line 2 into the upper part of the column C1. The solvent introduction temperature is, e.g., 50° to 90° C. The solvent flow can be in a weight ratio of 3 to 15 kg/kg with the charge flow. The column C1, e.g., operates with a bottom temperature of 90° to 140° C. The head temperature is 30° to 70° C.

The solvent leaving at the head by the line 3 mainly consists of isobutane and n-butane and possibly a little 1-butene and isobutene, as a function of the column setting. After condensation, a fraction of the distillate is returned as reflux to the column C1 by the line 4. The remainder of the effluent is collected by the line 5 and can, e.g., be passed to the pool C4.

The highly butane-depleted column bottom residue is passed by the line 6 to the lower part of the desorption column C2 under a pressure close to that of the column C1. The bottom temperature of the column C2, which is lower than the temperatures at which the solvent starts to deteriorate, is regulated so as to bring about a partial desorption of the butenes. It is, e.g., 150° to 170° C. The head temperature can be 30° to 60° C.

The effluent leaving at the head by the line 7 essentially consists of 1-butene and 2-butenes, as well as possibly a small isobutene proportion. It is condensed and partly returned as reflux to column C2 by the line 8. The remainder of the effluent is collected by the line 9.

The bottom residue of column C2 passing out via line 10 consists of a solvent flow still containing a fraction of butenes, e.g., 3 to 5% by weight. It is fed to the upper part of the purification column C3 operating at a pressure close to 1 bar (e.g., 0.7 to 1.5 bars) and between a bottom temperature of 140° to 170° C. and a head temperature of 120° to 150° C. The effluent leaving the head of the column C3 by the line 11 is partly condensed.

The liquid phase is returned as reflux from the reflux flask B to the column C3 by the line 12. The vapor phase essentially consists of butenes and contains a small proportion (e.g., 3 to 6% by weight) of solvent and is passed by the line 13 to a compressor K, in which it is raised to the pressure of the column C2 before being introduced by the line 14 into the lower part of said column C2.

The column bottom residue leaving by the line 15 is substantially pure solvent. It is recycled to the extractive distillation column C1. The thermal energy transported by this solvent flow, generally at a temperature of 150° to 170° C., can be partly used for heating the bottom of the column C1 via the exchanger E1 and partly for reheating the charge to its bubble point via the exchanger E2. The solvent flow can be cooled through the exchanger E3 before being passed by the pump P and the line 16 into the column C1. A topping up of solvent can take place by the line 17.

By means of the process according to the invention, it is possible to obtain butenes with a degree of purity of, e.g., approximately 97% by weight or higher if necessary, mainly as a function of the solvent proportion used and the efficiency (number of trays) of the extractive distillation column.

In the present description, the pressures given are absolute pressures, 1 bar=0.1 MPa.

A practical example of the inventive process will now be given.

EXAMPLE

The charge to be treated has the composition given in the second column of the table. The solvent used is anhydrous dimethyl formamide with a purity better than 99.8%. The columns used have the following characteristics:

The extractive distillation column C1 is a diameter 50 mm steel column having 100 overflow perforated trays.

The desorption column C2 is a diameter 50 mm steel column having 20 overflow perforated trays.

The purification column C3 is a diameter 50 mm glass column having 10 overflow perforated trays.

The three columns are made adiabatic by a heat loss compensation system for the steel columns and by a thermal insulation for the glass column.

Hereinafter will be given the operating conditions for the columns and the characteristics of the material flow. For each column the trays are counted from top to bottom.

The column C1 operates under an average pressure of 5.6 bars and is supplied at the 62nd tray by the charge at 50° C., with a flow rate of 436 g/h, and by solvent from the column C3 at 65° C. The solvent enters at the tenth tray at a rate of 2814 g/h. A distillate reflux representing 930 g/h is supplied to the column head. The flow rate and composition of the head effluent after condensation (distillate) are given in the third column of the table.

|  | Column C1 | | Column 2 | |
| --- | --- | --- | --- | --- |
|  | Charge | Distillate | Distillate | Residue |
| Flow rate g/h | 436 | 128 | 307 | 2928 |
| Composition % by weight | | | | |
| Isobutane | 18.37 | 62.18 | 0.02 | — |
| n-butane | 10.45 | 30.18 | 2.19 | 0.02 |
| 1-butene | 23.33 | 7.19 | 30.08 | 0.87 |
| Isobutene | 1.54 | 0.38 | 2.03 | 0.06 |
| Trans 2-butene | 27.91 | 0.06 | 39.57 | 1.59 |
| Cis 2-butene | 18.40 | 0.01 | 26.11 | 1.16 |
| DMF | — | <0.01 | <0.01 | 96.30 |

Column C2 functions at an average pressure of 5.4 bars and is supplied at the 18th tray by the preceding residue and at the 20th tray at 130° C. by 114 g/h of the vapor effluent of the purification column C3 (recycling), previously compressed to 5.5 bars. A distillate reflux of 130 g/h is established. The flow rate and composition of the head effluent after condensation (distillate), as well as those of the residue are given respectively in columns 4 and 5 of the table.

The column C3 operates under atmospheric pressure and is supplied at the first tray at 140° C. by the residue of the preceding column. A liquid reflux of 200 g/h is established, resulting from the partial condensation of the head effluent. The vapor fraction of the head effluent is recycled to column C2, as stated hereinbefore. At the bottom of column C3 collection takes place of quasi-pure DMF, which is returned to the column C1.

We claim:

1. In a process for the separation of butanes and butenes from a charge containing the same, comprising introducing said charge into an extractive distillation column under pressure and in contact with a polar solvent and withdrawing overhead product consisting essentially of butanes from the head of the extractive distillation column, the improvement comprising:

feeding resultant residue, comprised mainly of the solvent and butenes, collected at the bottom of the extractive distillation column into a desorption column operating under a pressure of 4–10 bars to partially desorb said butenes;

withdrawing resultant desorbed butenes from the head of the desorption column;

withdrawing resultant polar solvent residue containing a fraction of butenes from the bottom of the desorption column and feeding the withdrawn residue into a purification column operating under a pressure of approximately 1 bar;

withdrawing from said purification column a head effluent containing butenes and a fraction of the solvent;

partially condensing said head effluent, returning resultant condensate as reflux to the purification column, compressing uncondensed vapor phase, and returning resultant compressed vapor phase into the pressure desorption column; and withdrawing resultant purified solvent from the bottom of the purification column and recycling the purified solvent to the extractive distillation column.

2. A process according to claim 1, wherein the polar solvent is monomethyl formamide, dimethyl formamide, diethyl formamide, dimethyl acetamide, or n-methyl pyrrolidone.

3. A process according to claim 1, wherein the extractive distillation column operates at a pressure of 4 to 10 bars; the solvent is introduced into the upper part of said extractive distillation column at a flow ratio by weight of 3 to 15 to the flow of said charge; and the distillation column bottom temperature is 90° to 140° C. and the distillation column head temperature is 30° to 70° C.

4. A process according to claim 1, wherein the butenes obtained, have a purity of at least 97% by weight.

5. In a process for the separation of butanes and butenes from a charge containing the same, comprising introducing said charge into an extractive distillation column under pressure and in contact with a polar solvent and withdrawing overhead product consisting essentially of butanes from the head of the extractive distillation column, the improvement comprising:

feeding resultant residue, comprised mainly of the solvent and butenes, collected at the bottom of the extractive distillation column into a desorption column under pressure to partially desorb said butenes;

withdrawing resultant desorbed butenes from the head of the desorption column;

withdrawing resultant polar solvent residue containing a fraction of butenes from the bottom of the desorption column and feeding the withdrawn residue into a purification column under a pressure of approximately atmospheric pressure;

withdrawing from said purification column a head effluent containing butenes and a fraction of the solvent;

partially condensing said head effluent, returning resultant condensate as reflux to the purification column, compressing uncondensed vapor phase, and returning resultant compressed vapor phase into the pressure desorption column, and withdrawing resultant purified solvent from the bottom of the purification column and recycling the purified solvent to the extractive distillation column, wherein the desorption column pressure is 4 to 10 bars, the desorption column bottom temperature, being below the decomposition temperature of the solvent, is 150° to 170° C. and the desorption column head temperature is 30° to 60° C.

6. A process according to claim 5, wherein the polar solvent residue from said desorption column contains a major proportion of solvent and 3 to 5% by weight butenes.

7. In a process for the separation of butanes and butenes from a charge containing the same, comprising introducing said charge into an extractive distillation column under pressure and in contact with a polar solvent and withdrawing overhead product consisting essentially of butanes from the head of the extractive distillation column, the improvement comprising:

feeding resultant residue, comprised mainly of the solvent and butenes, collected at the bottom of the extractive distillation column into a desorption column under pressure to partially desorb said butenes;

withdrawing resultant desorbed butenes from the head of the desorption column;

withdrawing resultant polar solvent residue containing a fraction of butenes from the bottom of the desorption column and feeding the withdrawn residue into a purification column under a pressure of approximately atmospheric pressure;

withdrawing from said purification column a head effluent containing butenes and a fraction of the solvent;

partially condensing said head effluent, returning resultant condensate as reflux to the purification column, compressing uncondensed vapor phase, and returning resultant compressed vapor phase into the pressure desorption column; and withdrawing resultant purified solvent from the bottom of the purification column and recycling the purified solvent to the extractive distillation column, wherein the pressure of the purification column is approximately 1 bar, the purification column bottom temperature is 140° to 170° C. and the purification column head temperature is 120° to 150° C.

8. A process according to claim 7, wherein resultant head effluent from said purification column comprises a major proportion of butenes and 3 to 6% by weight solvent.

9. In a process for the separation of butanes and butenes from a charge containing the same, comprising introducing said charge into an extractive distillation column under pressure and in contact with a polar solvent and withdrawing overhead product consisting essentially of butanes from the head of the extractive distillation column, the improvement comprising:

feeding resultant residue, comprised mainly of the solvent and butenes, collected at the bottom of the extractive distillation column into a desorption column under pressure to partially desorb said butenes;

withdrawing resultant desorbed butenes from the head of the desorption column;

withdrawing resultant polar solvent residue containing a fraction of butenes from the bottom of the desorption column and feeding the withdrawn residue into a purification column under a pressure of approximately atmospheric pressure;

withdrawing from said purification column a head effluent containing butenes and a fraction of the solvent;

partially condensing said head effluent, returning resultant condensate as reflux to the purification column, compressing uncondensed vapor phase, and returning resultant compressed vapor phase into the pressure desorption column; and withdrawing resultant purified solvent from the bottom of the purification column and recycling the purified solvent to the extractive distillation column, wherein the extractive distillation column operates at a pressure of 4 to 10 bars, the solvent is introduced into the upper part of said extractive distillation column at a flow ratio by weight of 3 to 15 to the flow of said charge, the distillation column bottom temperature is 90° to 140° C., and the distillation column head temperature is 30° to 70° C. and whrein the desorption column pressure is 4 to 10 bars, the desorption column bottom temperature, being below the decomposition temperature of the solvent, is 150° to 170° C. and the desorption column head temperature is 30° to 60° C.

10. In a process for the separation of butanes and butenes from a charge containing the same, comprising introducing said charge into an extractive distillation column under pressure and in contact with a polar solvent and withdrawing overhead product consisting essentially of butanes from the head of the extractive distillation column, the improvement comprising:

feeding resultant residue, comprised mainly of the solvent and butenes, collected at the bottom of the extractive distillation column into a desorption column under pressure to partially desorb said butenes;

withdrawing resultant desorbed butenes from the head of the desorption column;

withdrawing resultant polar solvent residue containing a fraction of butenes from the bottom of the desorption column and feeding the withdrawn residue into a purification column under a pressure of approximately atmospheric pressure;

withdrawing from said purification column a head effluent containing butenes and a fraction of the solvent;

partially condensing said head effluent, returning resultant condensate as reflux to the purification column, compressing uncondensed vapor phase, and returning resultant compressed vapor phase into the pressure desorption column; and withdrawing resultant purified solvent from the bottom of the purification column and recycling the purified solvent to the extractive distillation column, wherein the extractive distillation column operates at a pressure of 4 to 10 bars, the solvent is introduced into the upper part of said extractive distillation column at a flow ratio by weight of 3 to 15 to the flow of said charge, the distillation column bottom temperature is 90° to 140° C., and wherein the pressure of the purification column is approximately 1 bar, the purification column bottom temperature is 140° to 170° C. and the purification column head temperature is 120° to 150° C.

11. In a process for the separation of butanes and butenes from a charge containing the same comprising introducing said charge into an extractive distillation column under pressure and in contact with a polar solvent and withdrawing overhead product consisting essentially of butanes from the head of the extractive distillation column, the improvement comprising:

feeding resultant residue, comprised mainly of the solvent and butenes, collected at the bottom of the extractive distillation column into a desorption column under pressure to partially desorb said butenes;

withdrawing resultant desorbed butenes from the head of the desorption column;

withdrawing resultant polar solvent residue containing a fraction of butenes from the bottom of the desorption column and feeding the withdrawn residue into a purification column under a pressure of approximately atmospheric pressure;

withdrawing from said purification column a head effluent containing butenes and a fraction of the solvent;

partially condensing said head effluent, returning resultant condensate as reflux to the purification column, compressing uncondensed vapor phase, and returning resultant compressed vapor phase into the pressure desorption column; and withdrawing resultant purified solvent from the bottom of the purification column and recycling the purified solvent to the extractive distillation column, wherein the desorption column pressure is 4 to 10 bars, the desorption column bottom temperature, being below the decomposition temperature of the solvent, is 150° to 170° C. and the desorption column head temperature is 30° to 60° C. and wherein the pressure of the purification column is approximately 1 bar, the purification column bottom temperature is 140° to 170° C. and the purification column head temperature is 120° to 150° C.

12. A process according to claim 11, wherein resultant head effluent from said purification column comprises a major proportion of butenes and 3 to 6% by weight solvent.

13. A process according to claim 12, wherein the butenes obtained have a purity of at least 97% by weight.

* * * * *